United States Patent [19]
Blendl

[11] Patent Number: 5,355,400
[45] Date of Patent: Oct. 11, 1994

[54] COMPENSATING FILTER FOR THORAX X-RAY PHOTOGRAPH

[75] Inventor: Christian Blendl, Bergheim, Fed. Rep. of Germany

[73] Assignee: Agfa-Gevaert Aktiengesellschaft, Leverkusen, Fed. Rep. of Germany

[21] Appl. No.: 51,889

[22] Filed: Apr. 26, 1993

[30] Foreign Application Priority Data

May 4, 1992 [DE] Fed. Rep. of Germany ....... 4214742

[51] Int. Cl.⁵ ................................................ G21K 3/00
[52] U.S. Cl. ...................................... 378/156; 378/145
[58] Field of Search ................. 378/156, 157, 158, 159

[56] References Cited

U.S. PATENT DOCUMENTS 2,630,536  3/1953  Vladeff ............................ 378/159
5,056,128  10/1991  Thompson ...................... 378/156

FOREIGN PATENT DOCUMENTS 3217423  11/1983  Fed. Rep. of Germany .

Primary Examiner—Craig E. Church
Attorney, Agent, or Firm—Connolly and Hutz

[57] ABSTRACT

A device for compensating large absorption differences when photographing the thorax by means of X-ray radiation, whereby a compensating filter is placed close to the X-ray tube in the beam of the X-ray tube perpendicular to the optical axis of the X-ray radiation, whereby a support running in the direction of the optical axis is placed on the X-ray tube housing above the optical axis at an angle of 93° to 105° to the vertical, at which a filter holder, which can be displaced in the direction of the support, is arranged with the compensating filter, allowing optimum matching of the compensating filter to each patient.

10 Claims, 3 Drawing Sheets

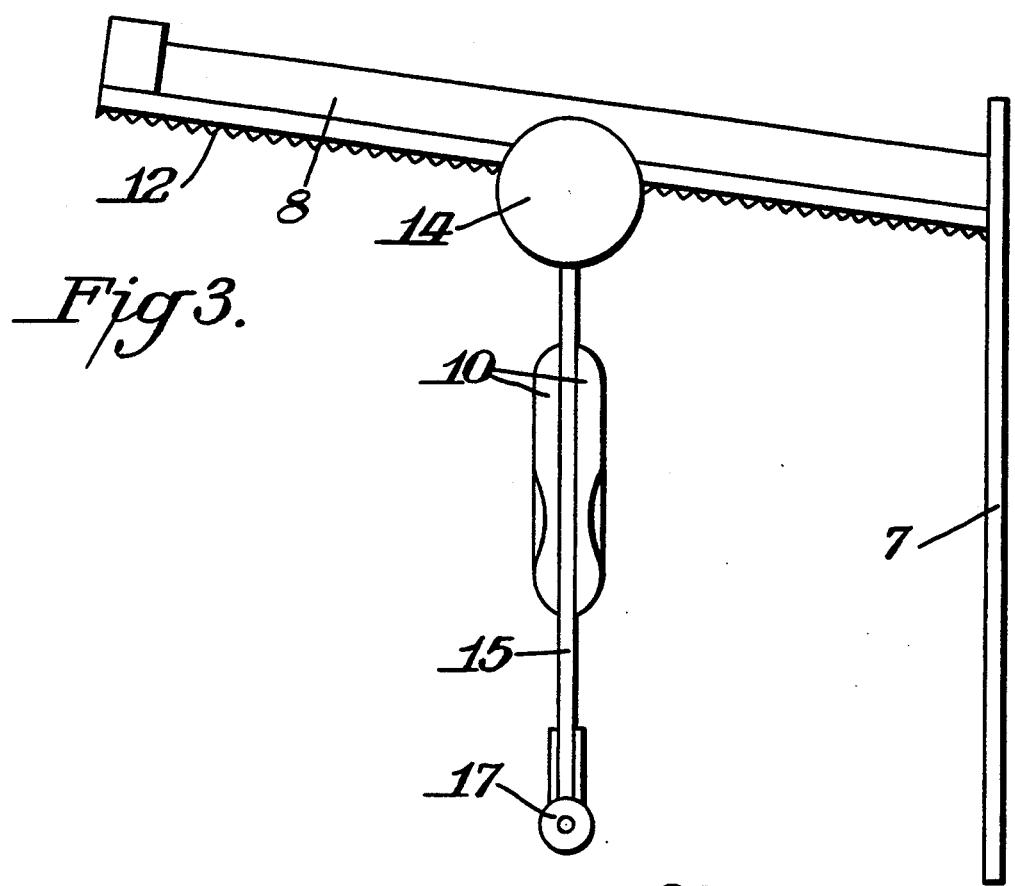
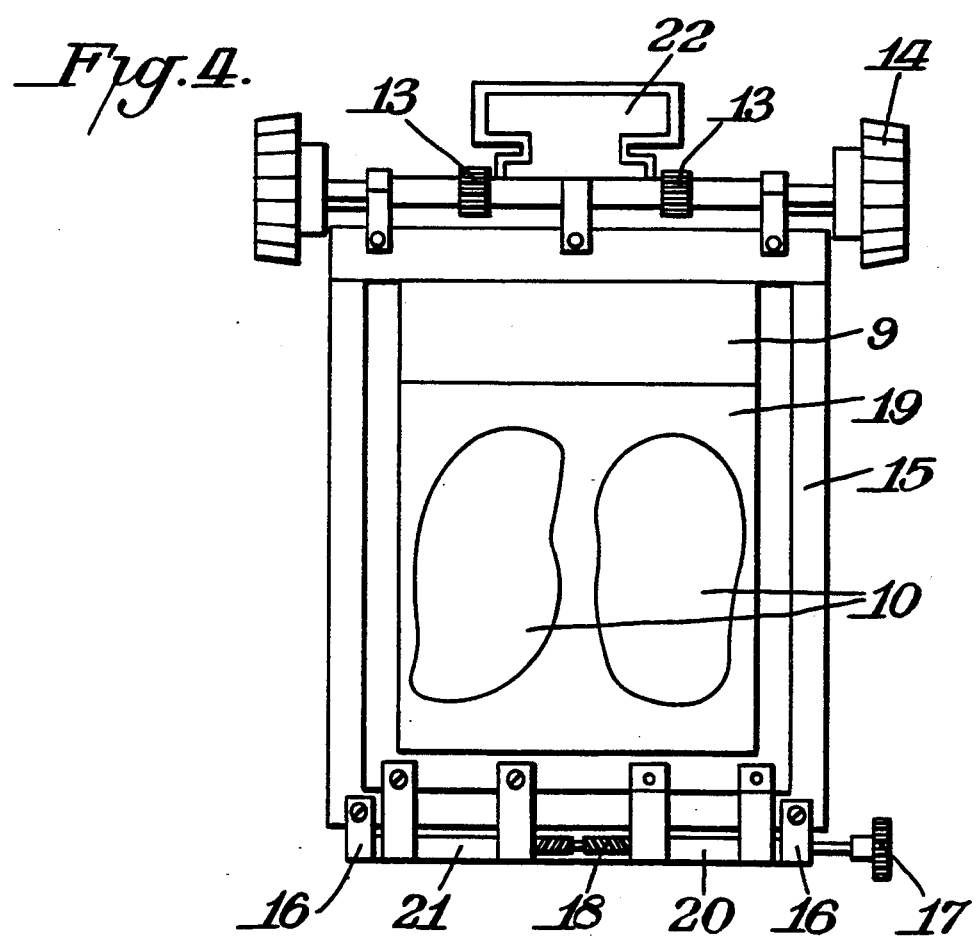

COMPENSATING FILTER FOR THORAX X-RAY PHOTOGRAPH

The invention concerns a device for compensating large absorption differences when photographing the thorax by means of X-ray radiation, whereby a compensating filter that is matched to the anatomical conditions of the subject is placed close to the X-ray tube in the beam of the X-ray tube perpendicular to the optical axis of the X-ray radiation.

Compensating filters for X-ray diagnosis, especially for photographing the thorax, are for example known from DE-A 32 17 423 and the literature cited therein.

These compensating filters consist for example of aluminium and are placed in the beam of the X-ray tube by means of a holder close to the X-ray tube. These filters are matched to the anatomical shape of the subject, e.g. the lungs. The filter attenuates the X-ray beam so that with precise exposure of the lung section the denser parts of the area surrounding the lungs are no longer under-exposed, or with precise exposure of the latter the lung section is no longer over-exposed.

Previous devices which contain such a filter are placed at a fixed distance from the housing of the X-ray tube, that is small in comparison to the distance of the X-ray tube from the patient. At best, the known devices permit very little matching between the filter and the individual differences in patients with regard to the size and exact position of the lobes. Depending on the patient, frequently either parts of the lungs are exposed to the unfiltered X-ray beam or parts of the area surrounding the lungs are only penetrated by an X-ray beam that is attenuated by the filtering arrangement, thereby causing faulty exposure in these partial areas of the type quoted above.

The aim of the invention is to remove these drawbacks and provide a device with which the filters can be optimally adjusted for each patient.

The aim is met with a device of the type cited above, which is characterised in that a support running in the direction of the X-ray cassette is placed on the X-ray tube housing above the optical axis at an angle of 93° to 105°, at which a filter holder, which can be displaced in the direction of the support, is arranged with the compensating filter.

In a preferred practical form the filter holder consists of a frame in which two plates (a) and (b), one having the partial filter for the left-hand and the other the partial filter for the right-hand lobe, are arranged one above the other so that the distance between the two partial filters can be varied horizontally and perpendicularly to the optical axis.

In a further preferred practical form the partial filters, which can usually be up to 10 mm thick, are arranged on the two plates so that the partial filter on the plate (a) positioned nearest to the tube housing is arranged on the surface of the plate (a) that is pointing towards the tube housing and the partial filter on the plate (b) farthest from the tube housing is arranged on the surface of the plate (b) that is farthest from the tube housing.

The filter can consist of any material that is suitable for attenuating the X-ray beam. The filter preferably consists of aluminium.

The filter holder can be moved on the support by means of a rack-and-pinion drive or by means of a slide. Both the plates carrying the partial filters can be moved in particular by means of a contra-rotating screw.

Due to the support deviating very little from the horizontal, this means that the top edge of the filter remains at a more or less constant distance from the upper edge of the image, irrespective of the distance from the tube housing; the enlarged image of the filter affects only the lower regions of the lobes. Thus the different sizes of various patients can be taken into account in an anatomically correctly-matched manner.

In addition, matching to different widths of thorax is made possible by the ability of the filter to be displaced transversally.

Due to the combination of both displacement facilities, distinctly improved matching to anatomical conditions can be obtained compared to conventional filter designs.

The invention is explained in more detail by FIGS. 1 to 4:

FIG. 3 shows a side view of the device according to the invention.

FIG. 4 shows a front view of the filter holder.

Figure 1:
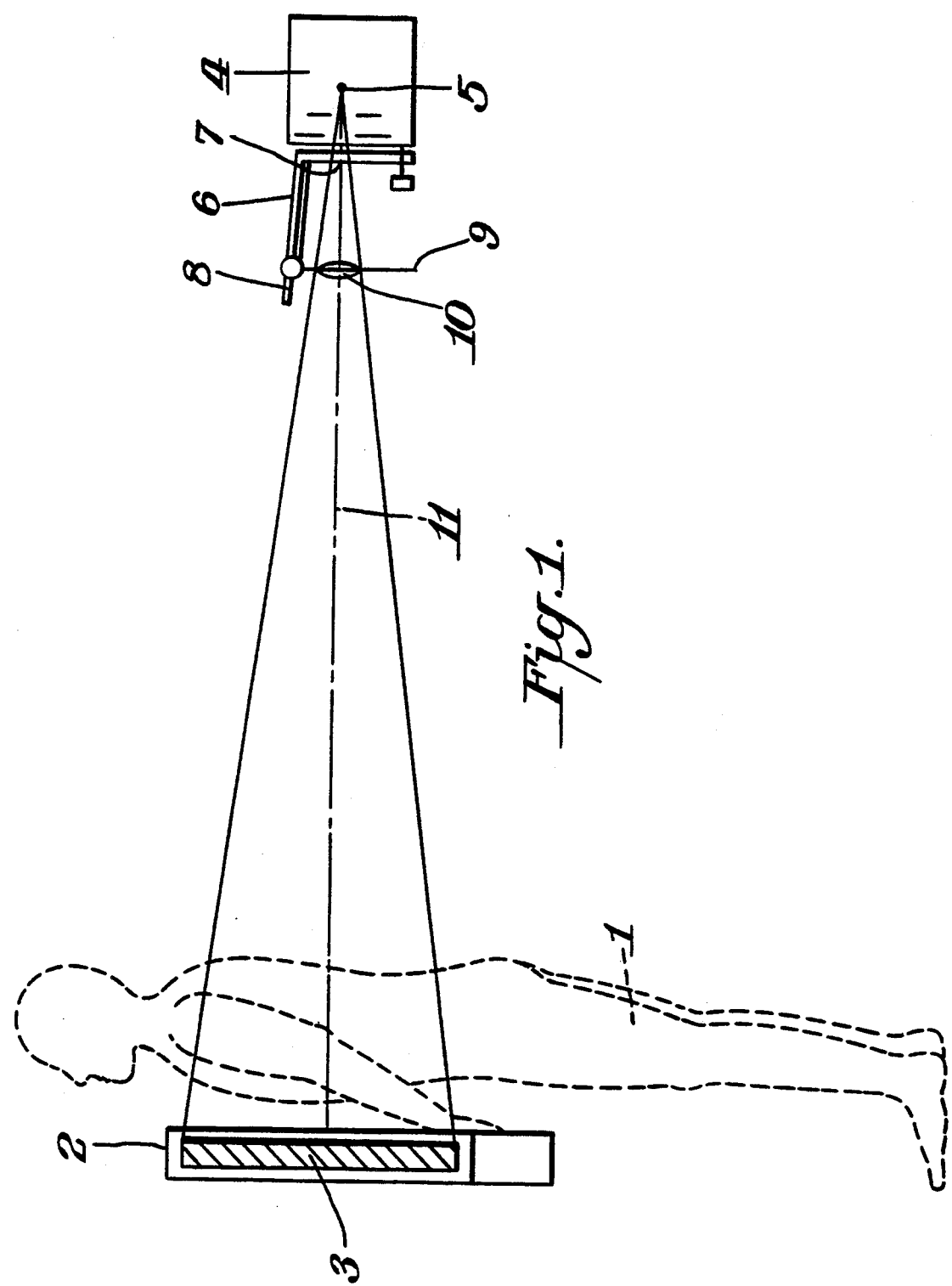
FIG. 1 shows in sketch form the arrangement of the device according to the invention during an X-ray photograph.

In FIG. 1 the patient (1) stands in front of the wall-mounted screen (2) with X-ray cassette (3) inserted. (4) denotes the X-ray tube housing with the focussed spot (5), in front of which the device (6) according to the invention with base plate (7), support (8), filter holder (9) and filter (10) is positioned. The optical axis of the X-ray apparatus is denoted by (11).

The distance between the focussed spot and the X-ray cassette is usually 1.5 to 2 meters. The base plate is used to attach the support and filter holder to the X-ray tube housing by the usual fastenings.

Figure 2:
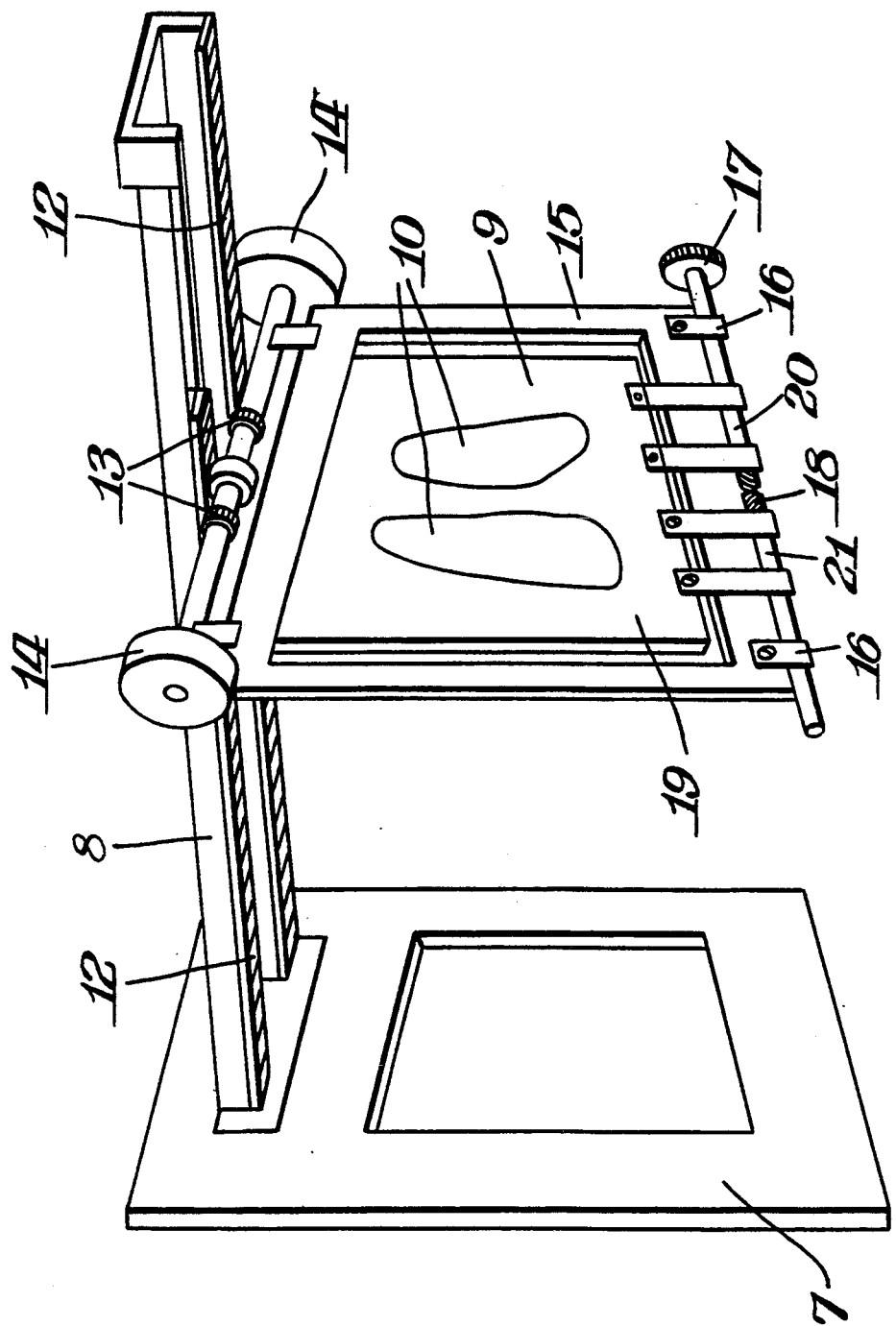
FIG. 2 shows a perspective view of the device according to the invention.

FIG. 2 shows the device according to the invention with base plate (7), support (8), filter holder (9) and the filter (10). There are toothed racks (12) on the support (8), via which the filter holder (9), which has toothed wheels (13) and adjusting screws (14), can be displaced. The filter holder (9) has an element (not shown) which forms a moving link between it and the support (8). The filter holder (9) consists of a frame (15) to which a screw (18) fitted with an adjusting screw (17) is attached by means of fasteners (16), one half of said screw having a left-hand thread and the other half a right-hand thread. In the frame (15) two plates (19) are arranged one above the other so that their top edges are free to move in a groove in the frame (15) and the lower edge of one of the plates is connected via the fastener (20) to the screw section with the right-hand thread and the lower edge of the other plate is connected via the fastener (21) to the screw section of the screw (18) with the left-hand thread. By rotating the adjusting screw (17) the two plates (19), each of which carries a partial filter of the lung filter (10), are displaced horizontally with respect to each other and perpendicularly to the optical axis.

FIG. 3 shows the base plate (7), the support (8) that makes an angle of 93° to 105° to the base plate, and which has toothed racks (12), one of which is shown, via which the frame (15) is moved by means of adjusting screws (14). The two partial filters of the lung filter (10) are shown on the right and the left of the frame.

FIG. 4 shows the filter holder (9) with toothed wheels (13), adjusting screws (14), frame (15), plates (19), lung filters (10), screw (18), adjusting screw (17) and the fasteners (16, 20, 21) by means of which the two plates (19) can be displaced with respect to each other in the frame (15). A element (22) by means of which the filter holder (9) can be displaced in a groove in the support (8), is attached to the filter holder (9).

What is claimed is:

1. A compensating filter device for use in an X-ray photographic apparatus having an X-ray tube in a housing, said compensating filter device comprising:
   a filter comprising a plate formed at least in part from a material which attenuates an X-ray beam;
   a filter holder which retains the filter in fixed position within said X-ray beam, and
   a support secured to said X-ray photographic apparatus and supportingly connected to said filter holder, said support comprising a horizontal member mounted to the X-ray tube housing and positioned in the direction of the optical axis of the X-ray beam, said support further characterized by being above the optical axis, and at an angle of 93° to 105° to the vertical, whereby the filter is precisely positioned within the X-ray beam to provide compensating X-ray beam attenuation.

2. A filter device as claimed in claim 1, wherein the X-ray attenuating material is aluminum.

3. A filter device as claimed in claim 1, wherein the support and filter holder are engaged by an adjusting means, whereby the distance between the X-ray tube and the filter holder are variable.

4. A filter device as claimed in claim 3, wherein the adjusting means comprises a toothed wheel on the filter holder which engages a toothed rack on the support.

5. A compensating filter device as claimed in claim 1, wherein the filter holder comprises a vertically and horizontally adjustable frame, whereby partial filters may be separately adjusted in the X-ray beam.

6. A filter device as claimed in claim 1, wherein the filter is a lung filter.

7. A filter as claimed in claim 6, wherein the lung filter comprises two partial filters.

8. A compensating filter device as claimed in claim 1, wherein the filter comprises two partial filters.

9. A filter device as claimed in claim 8, wherein each partial filter is held by at least one fastener to a screw having a unique thread pitch and thread direction, whereby the partial filter may be displaced horizontally with respect to each other and perpendicularly to the X-ray beam.

10. A device according to claim 8, wherein:
   the partial filters comprise plates with thickened beam attenuating portions,
   the filter holder is a frame, and
   the plates are arranged in the frame such that the thickened portion of the plate nearest the X-ray tube housing points toward the X-ray tube housing and the thickened portion of the plate farthest from the X-ray tube housing points away from the X-ray tube housing,
   whereby the thickened portions extend on either side of the frame.

* * * * *